United States Patent [19]

Della Posta et al.

[11] Patent Number: 4,847,090
[45] Date of Patent: Jul. 11, 1989

[54] CONFECTION PRODUCT AND METHOD FOR MAKING SAME

[75] Inventors: Joseph A. Della Posta, Stanhope; Anthony P. Piano, Sparta, both of N.J.

[73] Assignee: Warner-Lambert Company, Morris Plains, N.J.

[21] Appl. No.: 929,132

[22] Filed: Nov. 7, 1986

[51] Int. Cl.⁴ .................................................. A61K 9/48
[52] U.S. Cl. ...................................... 424/440; 424/441; 264/152; 425/296; 426/5; 426/103; 426/517; 426/518
[58] Field of Search ............... 424/440, 441; 427/3; 118/13, 15; 426/5, 103, 517, 518; 264/152; 425/296

[56] References Cited

U.S. PATENT DOCUMENTS

| | | | |
|---|---|---|---|
| 2,736,682 | 2/1956 | Hermelin | 424/471 |
| 3,274,992 | 10/1966 | Schneyer | 424/471 |
| 3,317,394 | 5/1967 | Fryklof et al. | 424/472 |
| 4,139,589 | 2/1979 | Beringer et al. | 264/131 X |
| 4,260,596 | 4/1981 | Mackles | 424/440 |
| 4,399,154 | 8/1983 | Puglia et al. | 426/5 |

Primary Examiner—Michael R. Lusignan
Attorney, Agent, or Firm—Gary M. Nath; Charles A. Gaglia, Jr.

[57] ABSTRACT

A confection piece having two or more discrete parts, each part being different from another in respect of at least one of its physical and/or chemical properties such as in respect of at least one or a combination of its coloration, material composition or texture. The confection piece can be used to combine diverse confections to provide new and unique organoleptic response for the user and its also can be used as a vehicle for oral administration of nutrients and medicinal compositions and particularly where same include interactive components which should be kept separated until the confection piece is dissolved in the user's mouth. A method for making the confection piece also is disclosed.

64 Claims, 5 Drawing Sheets

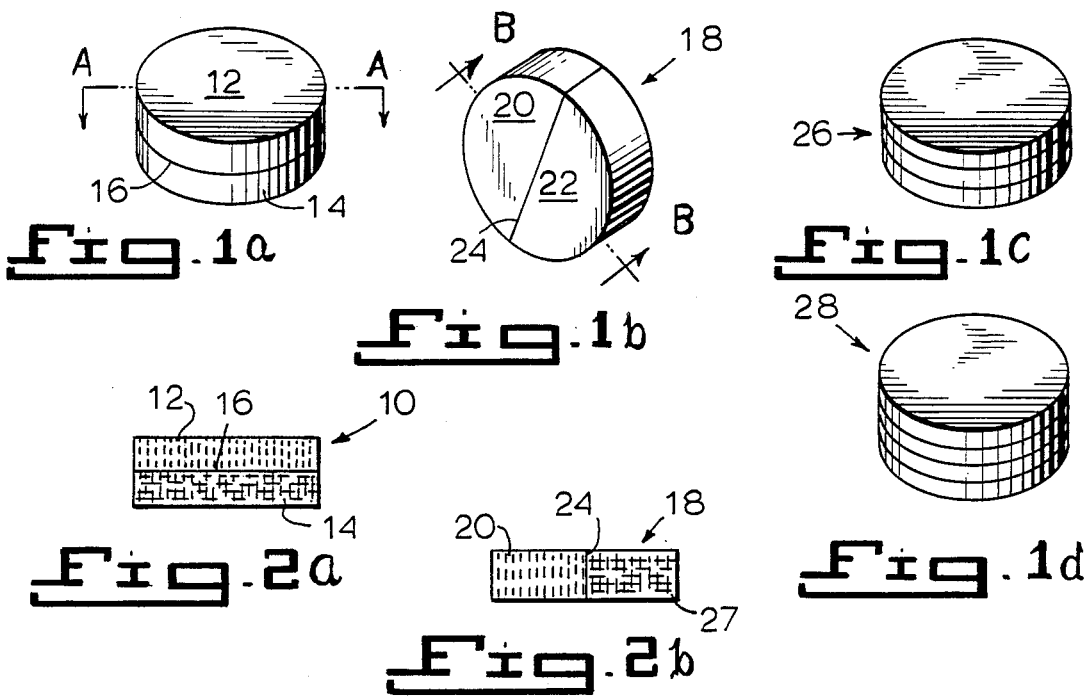
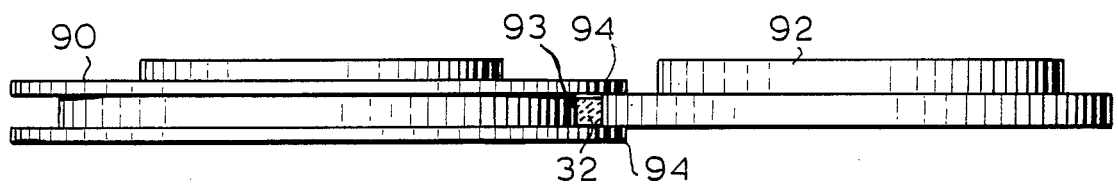
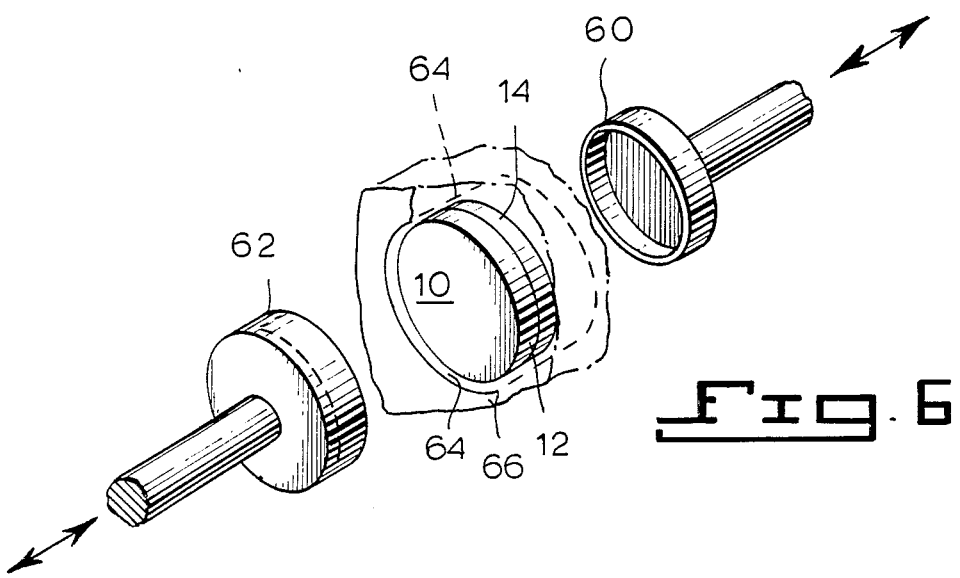

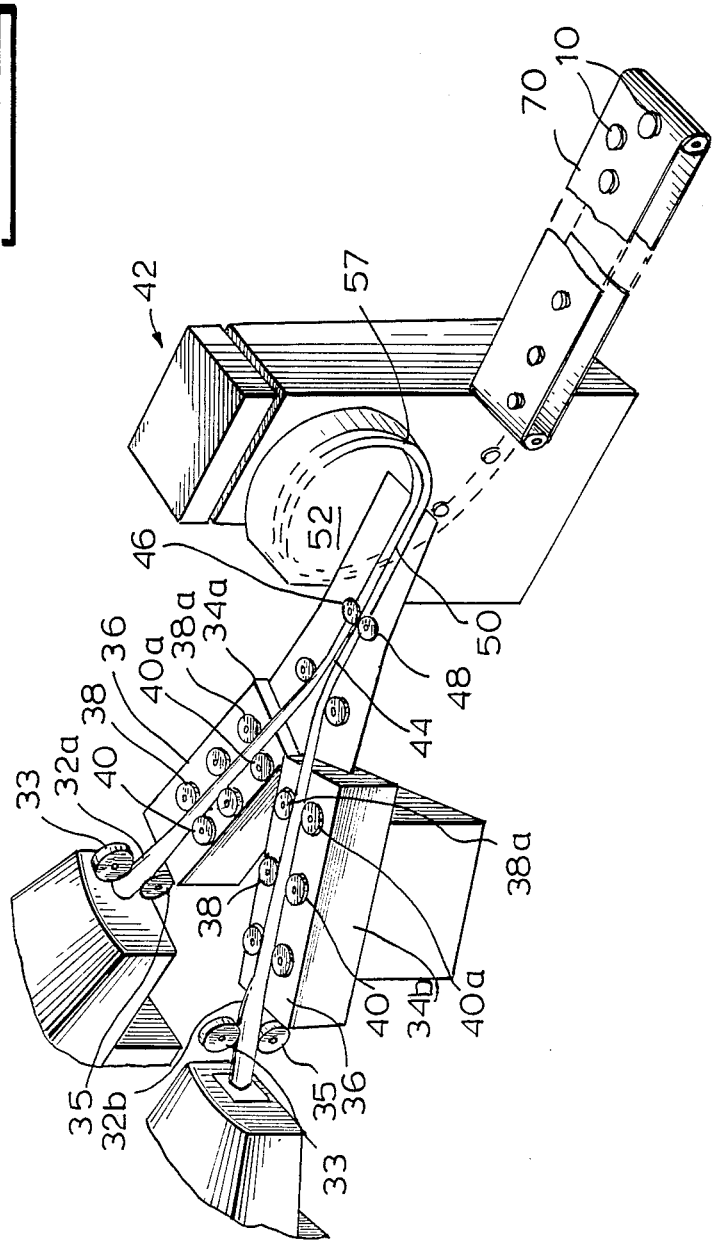

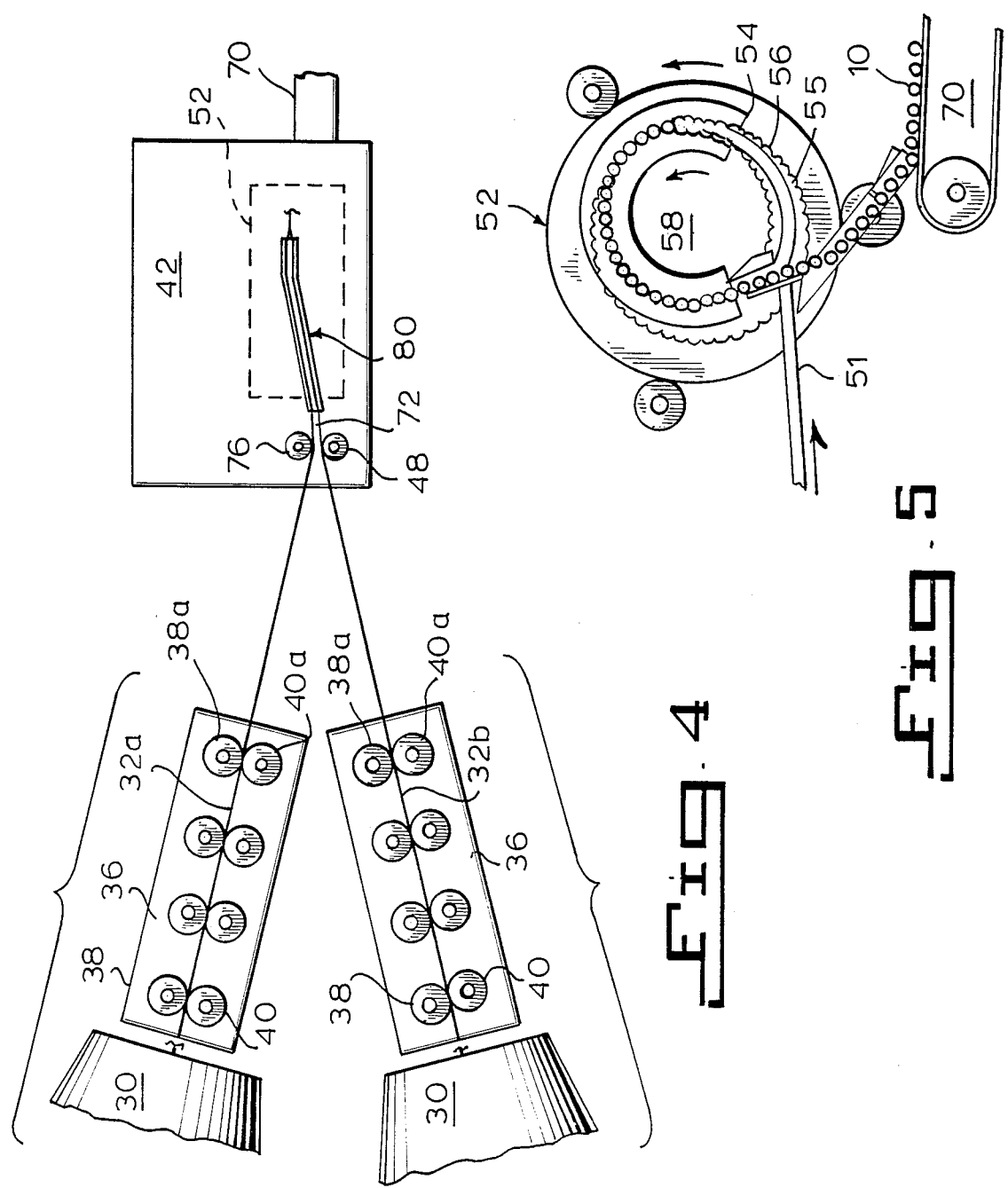

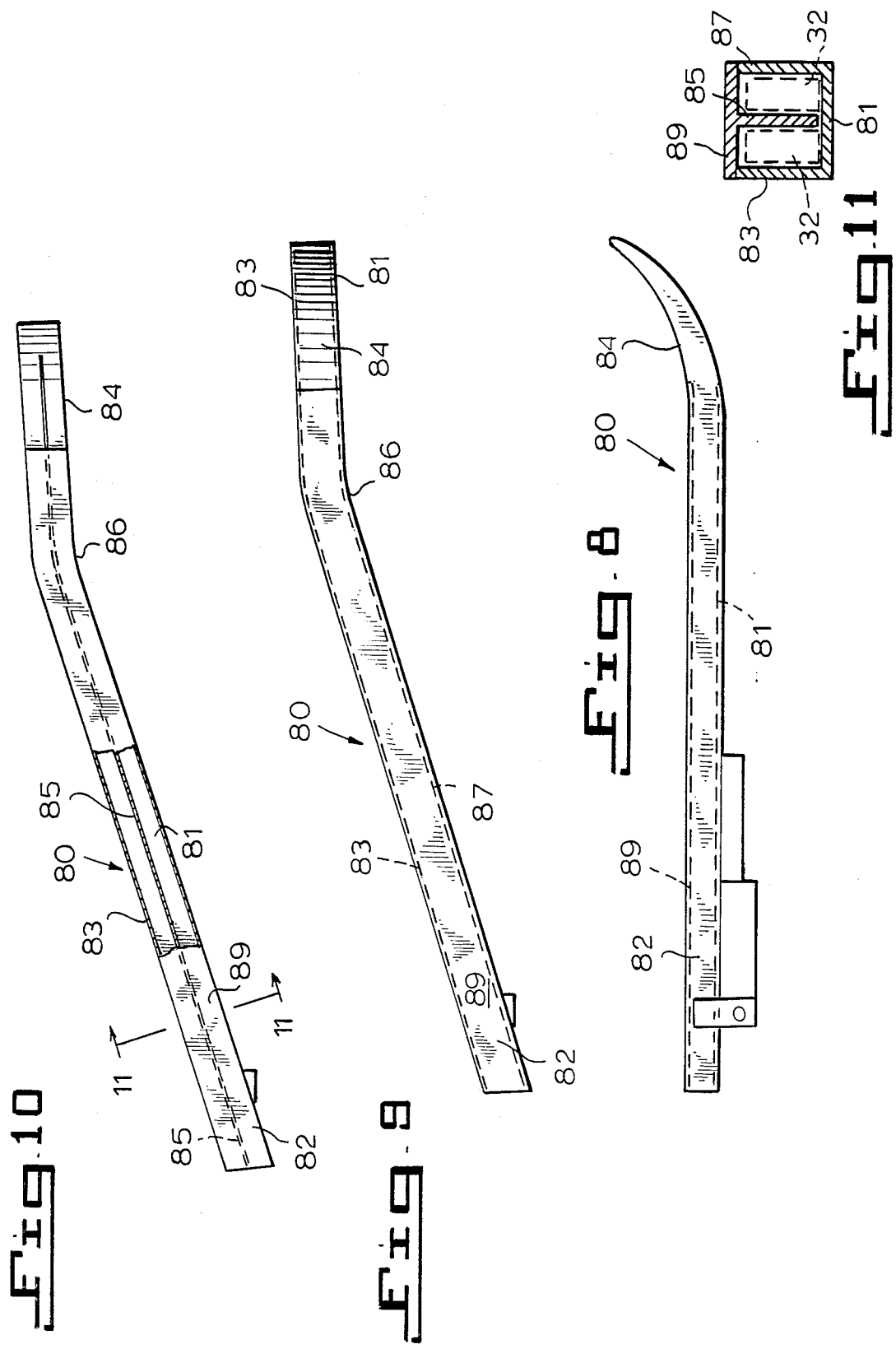

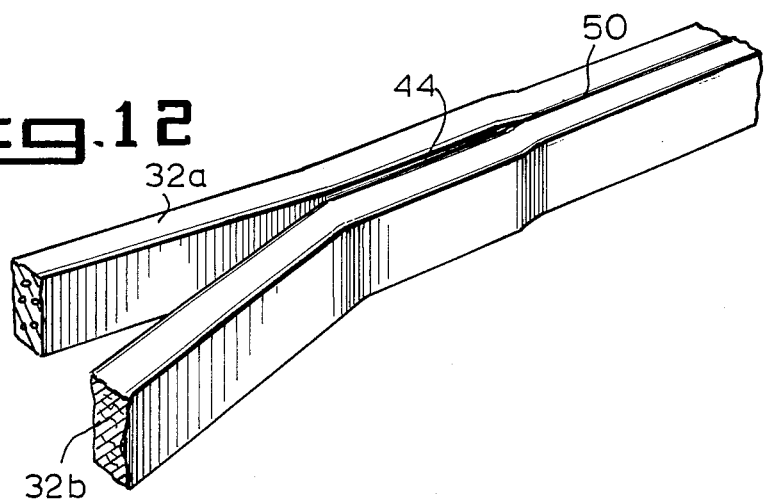
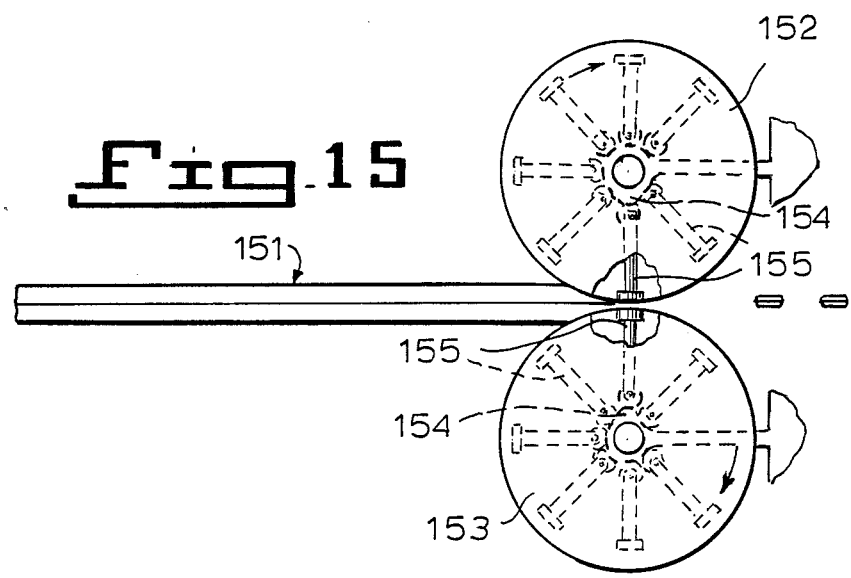
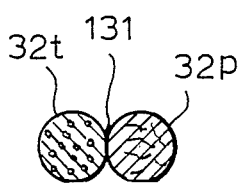
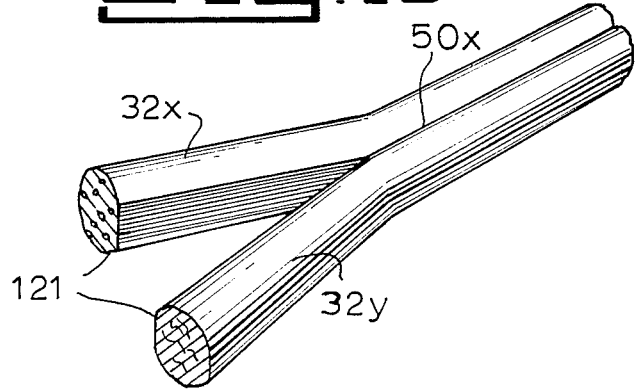

4,847,090

CONFECTION PRODUCT AND METHOD FOR MAKING SAME

BACKGROUND OF THE INVENTION

The present invention relates to an improved confection product which is characterized by embodiment in a single product body of discrete component parts at least certain of which differ from others in respect of their physical and/or chemical properties, i.e., the parts have differences of color, or composition, or texture or combinations of such so that the product may be given diverse and specifically distinct characteristics with regard to flavor, appearance, dissolution rate in the mouth, utilization as a vehicle or delivery system for oral administering of nutrients or medicaments and the like as well as others which allow for use of the product in numbers of unique forms.

One known manner of producing a two-layer confection product uses a double deposit method involving injection depositing of a first material layer in a mold followed by a second injection deposit on top of the first with the aim being to thereby obtain layer equality, i.e., provide for substantially equal product layer thicknesses. Such method has the disadvantage that the confection material temperature and viscosity must be controlled with precision as must the stroke of the injection piston feeding the mold. Even though the control functions are closely monitored in this procedure, there still results undesirable levels of product rejection in regard to layer equality as evidenced by a layer being noticeably thicker or thinner than intended and there frequently being incursion of one layer material into another. Also the production rate possible with this cyclic product making procedure is limited as compared to what might be possible if a continuous high speed making procedure could be employed in its place.

It also is desirable to be able to conveniently embody medicaments or nutrients in a confection base product since this is both an effective and generally innocuous mode by which a person can take various medicinal and nutrient compounds which might otherwise be thought unpleasant to ingest directly. One manner of delivery of antacids in a soft confection composition is described in commonly-assigned U.S. Pat. No. 4,545,989, the disclosure of which is incorporated herein by reference.

SUMMARY OF THE INVENTION

The present invention provides an edible confection product which by its shape and appearance has high consumer appeal in that it is comprised of two or more discrete layers or parts which can be used to provide heightened and differently pleasing organoleptic responses in the consumer. It also can serve as a vehicle for delivery of medicinal, nutrient and like substances in solid form for oral administration.

The confection product can be used for delivery of desired substances of types which normally are interactive one with another so that such substances can be maintained in non-contacting disposition one in one layer or part and others in other layers or parts until the product is ingested and delivery of these substances is initiated.

The edible article of the invention is of shaped body configuration comprised of at least two discrete body parts arranged in predetermined positioning one with respect to another and formed as the solidified product of corresponding ones of separate stocks of edible materials compressively plastic state cohered together in a single compression step along common joinder interfacing between each other, one body part being different from that of at least one other body part in respect of at least one of its physical and/or chemical properties.

The edible article can be made by advancing at least two separate plastic state continuous strands of edible material compositions from respective sources thereof along separate feed lines in passage directed toward a downstream article forming operation, the compositions in the respective sources being different one from another in respect of at least one of the physical and/or chemical properties of each, converging and guiding the travel passage of the advancing strands such as to bring said strands into closely alongside confrontation with each other and establish a predetermined orientation of one with respect to the other, forming a continuous strand composite by coheringly joining the advancing strands along a common strand interface by moving the strands into contact with each other while maintaining the prior established orientation therebetween, sectioning the composite in the forming operation to provide successive individual pieces thereof, and then shaping each piece into an article configuration having discrete parts arranged in positioning corresponding to the cohered strand orientation. The forming device will be one which acts crosswise to the composite joinder interface to compressively shape the article.

The invention provides article forming apparatus which includes means for forming plural plastic state strands of edible composition, means for shaping and advancing said strands toward an article forming operation, said shaping and advancing means imparting a predetermined advance orientation to said strands related to required entry dispositions thereof to an article forming device downstream of said shaping and advancing means, and strand orientation guidance means disposed between the shaping and advance means and the article forming device said guidance means effective to engageably guide and hold said strands in the said predetermined advance orientations thereof so that said strands enter the forming device undeviated from such orientations. The strand travel guidance is a chute extending from entry location of the forming device to proximal the sectioning means thereof, the chute including an initial length straight section and a curved fore length section for directing the strand into curved travel transition, the chute having side and top and bottom walls closely embracing the travelling strand to inhibit twisting of said strand from said orientation.

The apparatus may also include strand shaping means for shaping at least one continuous planar surface on each continuous strand prior to its cohering joinder to the other so that the strands can thereafter be juxtaposed alongside each other with the planar surface of one facing that of the other and cohered joinder be effected by merging said planar surfaces into face-to-face contact.

In accordance with the present invention, the improved edible, plural, discrete-layered confection product can be made by advancing at least two separate plastic state continuous strands of confection compositions from respective sources thereof along separate feed lines in passage directed toward a downstream article forming operation. The confection compositions can have various and diverse makeup as to each so that they could, for example, be hard candy types, chewy compositions such as nougats or chewing gum compositions, the essential difference being that one composition will differ in respect to another in regard to its physical and/or chemical properties. As used herein "physical and/or chemical properties" is intended to mean any one or a combination of coloration, ingredient composition or texture characteristics. Thus, it could be that two separate composition sources could have the same general hard candy ingredients but they would differ as to the flavoring or as to the colorants used in each. On the other hand the two compositions might have entirely different confection makeup in that one might be a hard candy composition, whereas the other would be a chewy composition, e.g., a nougat composition of the kind disclosed in B. W. Minifie, CHOCOLATE, COCOA AND CONFECTIONERY: Science and Technology, 2nd Edition, AVI Publishing Co., Inc., (Westport, Conn., (1980), at Pages 424–425. Moreover, the difference could be manifest by the simple variation that two otherwise identical makeup body parts vary in that one contains a medicinal component while the other does not.

The advancing plastic state strands will follow a converging and guided travel passage of each that will bring them closely alongside one another and in established orientation one with respect to another so that these strands can then be cohered together along a common strand interface to form a strand composite having such predetermined positioning of the strands as will be carried forward and reproduced in the ultimate formed confection product and the maintenance of that strand orientation is of consequential importance in the achievement of the purposes of the invention. Preferably, but not essentially, the strands will be subjected prior to cohering thereof, to a shaping operation to provide each with a continuous planar face surface so that the orientation established for these strands will present the strand planar surfaces in facing registered confrontation and it will then be at these planar surfaces that the eventual cohering strand joinder will occur.

The strand composite in a preferred forming operation feeds through a rotary forming machine of known type and in that machine it will because of its orientation and the operation of suitable sectioning devices, be sectioned into successive individual composite pieces with these pieces then being shaped by shaping die means into a particular shaped-body configuration and in particular a configuration of plural discrete body parts positioned in correspondence to the orientation arrangement of the composite strands. Preferably, but not essentially, the plural body parts will be of identical geometry and volume, e.g., two or more circular plan profile stacked or superposed layers compressively cohered along common interfaces. The shaped confection pieces are cooled as they pass from the forming machine, with the pieces being subjected to a cooling operation to solidify the piece layers or parts in unitary joinder and the pieces then move onto a suitable collection operation for further processing such as packaging.

When the confection piece is to be used as a vehicle for medicinal or nutrient delivery, these substances will be included in the source compositions. For example, one source can include vitamin C, while the other source will include a calcium carbonate. These respective and normally interactive substances thus will be present in the solidified and formed confection piece as one in one layer and the other in another layer, an arrangement keeping them apart until the confection piece is ingested following which they will be released as intended for the user's benefit. Incorporation of such types of medicinal and nutrient substances (and where no interactive problem is present) in one only of the confection piece layer or body parts is of course also contemplated.

The size and weight of the confection piece will vary depending on an intended end product purpose. Thus a two-layered, generally lozenge-shaped piece could weigh about 3 grams whereas, a confection piece for a lollipop shape could weigh as much as 20 grams. Correspondingly, strand size can vary as can its formed shape so that where two, rectangular sectional strands are employed the respective strand width could be one in a range of about ⅜ inch to about ½ inch and the height being in a range of about 1.5 times the width to about 0.5 times the width. A two-strand composite could have a width which is in the range of about 7/16 inch to about 13/16 inch and a height in the range of about 1.5 times the width to about 0.25 times the width.

The invention also provides for use in the known product forming machine and related apparatus employed for making the product of components relating to special shaping rollers for shaping the advancing strands to facilitate cohering contact of same and also of an improved form of a guidance chute positionable in the rotary forming machine to effect two-dimensional maintenance of strand or stranded composite predetermined orientation as same is entering the sectioning devices in the rotary forming machine.

The invention accordingly comprises the features of construction, arrangements of parts and steps as found in the respective confection piece, method for making same and improvements in forming apparatus as will be exemplified in the description hereinafter set forth and the scope of the invention will be indicated in the claims.

BRIEF DESCRIPTION OF THE DRAWINGS

A fuller understanding of the nature and objects of the invention will be had from the following detailed description taken in conjunction with the accompanying drawings in which:

FIG. 1a is a perspective view of a lozenge-shaped edible confection piece made in accordance with the principles of the present invention, the confection piece having two discrete body-parts arranged in predetermined positioning one with respect to another as discrete stacked or superposed layers of coextensive circular expanse, the material of one body part or layer being different than that in the other body part at least in respect of its coloration;

FIG. 1b is a perspective view of a confection piece similar to that shown in FIG. 1a except depicting a different predetermined positioning of the body parts with respect to each other;

FIGS. 1c and 1d are perspective views of further forms of confection pieces wherein same are configured, respectively, as three and four stacked layered, shaped-bodies having the respective three and four discrete body parts shown;

FIGS. 2a and 2b are sectional views as taken along the respective section lines A—A and B—B in FIGS. 1a and 1b and illustrate the discrete character or makeup of each body part of the confection articles which are cohered along common joinder interfacing between each other and made in accordance with the invention, the depicted confection pieces parts being different from each other at least in regard to the body part colorations, i.e., one body part is purple and the other body part is yellow;

FIG. 3 is a perspective view of apparatus with which confection pieces can be made in accordance with the present invention and wherein the two separate advancing confection strands are sized and shaped separately and then cohered together to form a plural stranded composite at entry to the rotary forming machine in which the composite is thereafter sectioned into individual pieces and the pieces shaped into desired individual article configuration;

FIG. 4 is a top diagrammatic plan view of the apparatus shown in FIG. 3 showing the alternative manner of maintaining the two separate advancing confection strands out of contact with each other until the arrival of same at the continuous length sectioning means carried in the rotary forming machine at which point they are cohered together to form the composite, there further being illustrated a strand guidance chute employed within the rotary forming machine to maintain the strands in a predetermined orientation thereof until same are coheringly joined and the section and forming devices of the rotary forming machine being depicted in dashed line block outline only;

FIG. 5 is a fragmentary elevational view illustrating in graphic manner, the functioning of the known type of rotary forming machine as it sections the composite into pieces and shapes these pieces into desired article shape;

FIG. 6 is a diagrammatic depiction of the functioning of the cooperating shaping dies mounted in the FIG. 5 machine as same shape a sectioned composite piece;

FIG. 7 is an elevational view showing a feed and shaping roller set which can be employed in the FIGS. 3 and 4 apparatus to shape the advancing strands into a desired strand cross-sectional shape, the depicted rollers being used to form a strand cross section of rectangular shape;

FIG. 8 is a side elevational view of one form of improved guidance chute which can be used in the forming apparatus and wherein the two advancing strands are cohered at entry to the rotary forming machine as is done in the FIG. 3 article making procedure;

FIG. 9 is a top plan view of the guidance chute shown in FIG. 8;

FIG. 10 is a top plan view of another chute embodiment wherein separate guide courses are provided therein for the separate strands and employed in the instance where the said separate strands enter the rotary forming machine each in predetermined orientation but are not cohered one with the other until just prior to their arrival at the sectioning means as is done in the FIG. 4 showing;

FIG. 11 is a sectional view as taken along the line 11—11 FIG. 10;

FIG. 12 is a perspective view illustrating the sequence of movements of the respective two advancing strands of rectangular section as same feed into converged, close alongside positioning one with the other and then merge to cohere along a common interface forming the plural strand composite from which the individual ultimate plural, discrete body parts confection pieces are made;

FIG. 13 is a perspective view similar to FIG. 12 except the cross-section of the strands is partly of planar shape with the remainder being generally circular;

FIG. 14 depicts in transverse section, the cohering of two circular section strands at a common tangent interface therebetween; and FIG. 15 is a top plan view showing another manner of forming the confection pieces wherein the plural strand composite is fed through another type of forming device wherein the individual confection pieces are punched out of the composite.

Throughout the following description like reference numerals are used to denote like parts in the drawings.

DESCRIPTION OF THE PREFERRED EMBODIMENTS

The present invention is concerned with a new and highly useful form of confection which may be embodied as an article per se, wherein it is proposed to provide the user with unusual and various taste pleasantry and organoleptic satisfaction, or it may be embodied as a confection based vehicle for containment therein of various medicinal preparations or nutrients intended for oral administration to a user for specified physiologic purpose. The confections or confection material compositions used can be many and varied but generally will be understood as being any one or a combination of hard candy confection, chewy confection and chewing gum, further general description of such being given next.

A hard candy confection can be one prepared from a mixture of sugar and other carbohydrates that are kept in an amorphous or glassy condition. This form can be considered a solid syrup of sugars generally having from 0.5 to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweeteners, acidulents, colorants and so forth may also be added. Hard candy may also be prepared from non-fermentable sugars such as sorbitol, mannitol, and hydrogenated corn syrup.

A chewy confection could for example be of the nougat compositions disclosed in the earlier mentioned Minifie reference, being made of soft confectionery materials. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7 g/cc. By comparison, the high boiling syrup, or "bob syrup," is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation.

With respect to chewing gum formulations, such will contain a gum base and various additives, such as sweeteners and flavors. The gum base employed will vary greatly depending on various factors such as the type of base used, consistency desired and other components used to make the final product. The chewing gum composition may additionally include the conventional additives of flavoring agents, coloring agents, emulsifiers and additional fillers.

The variations that one may practice with regard to these confections are wide ranging and within the ability of those skilled in the art particularly with regard to use of additional composition fillers, texture modifiers, flavoring components, use of coloring agents and the particularized involvements required for admixing or embodying medicinal, medicament and nutrient substances in effective manners in selected or given ones of confection compositions.

Referring now to FIGS. 1a–1d and 2a and 2b, various ones of the many possible embodiments of shaped body confection pieces which can be made in accordance with the invention are shown, the common characteristic of such products being that they each comprise at least two discrete layers or body parts arranged in predetermined positioning one with the other and further that at least one of the physical and/or chemical properties of one layer or part is different from that in another in respect of any one or a combination of its coloration, ingredient composition or texture. The depicted forms are all of generally circular planar profile body shape, being e.g., cylindrical but it will be understood that other shapes are contemplated such lozenge etc. FIG. 1a shows a confection piece 10 having two discrete body parts 12, 14 stacked in superposed positioning and being the solidified product of corresponding ones of separate material stocks compressively plastic state cohered together along common joinder interfacing 16. Each body part 12, 14 is of distinct layer character and it is as noted above materially different than the other layer. One manner of that difference is shown in FIG. 2a from which it is seen that body part 12 is of purple coloration, whereas body part 14 is of yellow coloration. The difference between the two body part material compositions may and need only be in regard to the coloration dyes used in each, the remaining ingredients otherwise being the same. The body part compositions also could be different in regard to the composition make up of each or in regard to the texture of the respective parts. In regard to composition texture, the layers or body parts 12, 14 could be of the same basic chewy confection composition disclosed, e.g., in U.S. Pat. No. 4,545,989 but that from which one body part is made could have different texture than the other as by addition of a gaining promoter such as 6X sugar thereto which would result in that layer having chew characteristics different than that of the other layer. Variation in consistency between the two layers wherein one material layer could be harder chewing than the other also could be exemplified in layer compositions of toffee, but toffees which are respectively harder and softer in chew character.

The confection piece 18 shown in FIG. 1b has two body parts 20, 22 formed along common interface 24 but rather than being positioned as stacked layers each is configured as a partly-cylindrical body part alongside facing the other body part, the interfacing being a diameter of a circle. In this body configuration, and if say three body parts were present, the interfacing would be along three equally spaced radii of the circle. These body parts are like those of the confection piece 10 different at least in respect of their coloration as shown in FIG. 2b. With two body part configurations it is convenient, though not essential that the respective body parts each comprise one-half of the geometric volume of the shaped body. FIGS. 1c and 1d illustrate other body configurations 26, 28 wherein these bodies are the respective three and four stacked, cohered layers or body parts arranged in the predetermined superposed and coextensive positionings shown.

It will be seen that these forms of body shapes readily lend to employment of same for eye-appealing variations in numerous combinations of colorations in sweet confection pieces per se, and also for variations in the compositional makeup of the body parts to evoke various and different pleasant organoleptic effects when the consumer chews or dissolves one in the mouth. It also is apparent that the confection piece is admirably suited to the end of being a vehicle for oral administration of certain other substances as will be dealt with next describing by way of example some of the wide range of delivery uses to which the confection piece can be adapted.

By way of illustration, confection piece 10 can be comprised of two discrete and separate confection compositions which produce most satisfying user response. One or both of these same two body parts also can also serve as a vehicle for delivering nutrient products in the concurrent candy piece ingestion process. Thus confection part 12 may contain in its composition vitamin C. Confection part 14 on the other hand may contain a user needed supplement such as calcium provided in the form of calcium carbonate. Under normal circumstances, vitamin C and calcium carbonate are interactive components and could not be contained in the same single vehicle composition since they would within that composition react one with the other to vitiate the intended separate and distinct administration of each at the time the vehicle was consumed.

With regard to certain medicinal compounds there are potential interactions which can be avoided with use of the discrete body part candy piece of the invention.

In the case of medicinal compounds, the following interactions may be avoided by multiple layer technology. Flavor-medicinal interactions such as antihistamines with aldehyde containing flavor components. Specific non-limiting examples are:

Anesthetics, such as benzocaine;

Antitussives, such as dextromethorphan, dextromethorphan hydrobomide, noscapine, carbetapentane citrate, and chlophedianol hydrochloride;

Antihistamines, such as chlorpheniramine maleate, phenindamine tartrate, pyrilamine maleate, doxylamine succinate, phenyltoloxamine citrate, diphenhydramine hydrochloride, promethazine, and triprolidine;

Antinauseants, such as dimenhydrinate, and meclizine;

Decongestants, such as phenylephrine hydrochloride, phenylpropanolamine hydrochloride, pseudoephedrine hydrochloride, ephedrine.

With aldehyde containing flavors, a non-limiting list of such flavors include: cherry, cinnamon, grape, grapefruit, lime, lemon, orange, raspberry, strawberry and the like.

Such interactions can be avoided by incorporating the flavor ingredient in one body part while the medicinal compound can be contained only in the other body part. Thus among the interactions which in likewise manner can be avoided in the delivery vehicle of the invention are the example of benzocaine, an anesthetic, with hexylresorcinol and the example of aspirin with basic compounds such as certain of the decongestants and antihistamines listed above.

Continuing reference now will be had to FIGS. 3–7 as description is given in detail of the new and advantageously high speed manner of making the confection pieces. In this confection piece making operation utilization is made of certain known apparatus which in certain respects has been improved in fulfillment of its use for production of the new candy piece. As can be seen from FIG. 3, known batch former units model 19, rope sizers model 165 and an automatic sweet-forming machine model Uniplast 160 all as manufactured and sold by the Hamac-Holler Div. of Robert Bosch GmbH of Viersen, West Germany are used. The batch former 30 is supplied with cooked and mixed stocks of the particular ones of the layer compositions which are to be used, those stocks having been subjected to mixing and kneading in conventional manner by manners and means well known to those skilled in the art. Further and in the instance where nutrient or medicinal compounds are to be incorporated in the confection piece parts, such incorporation will have been effected in and by the procedures known for such purpose. The batch formers 30 contain a number of cone rollers (not shown) which extrude the particular stocks as continuous plastic state extrudates or strands 32a, 32b, the strands being most commonly termed in the art as "ropes." The strands 32a, 32b feed onto the respective rope sizers 34a, 34b which include draw-off rollers 33, 35 to draw the strands out of the batch formers. The rope sizers include upper table sections 36 on which are mounted a number of sets of sizing roller pairs 38, 40 which serve to progressively diminish the strand diameters as they feed along the table section 36 to a strand in-feed frame 39 connecting the rope sizers 34a, 34b to the rotary forming machine 42 (the Uniplast). At least one of the roller pairs 38, 40 on the rope sizers can be employed for strand shaping and advance functions as will be described in more detail later on and one or more such roller pairs can be heated to further maintenance of the strand plastic state temperature at desired values. In connection with the shaping of the strands it is convenient to shape a planar face surface on the strands as this facilitates interface joinder. Such planar face surface could be, for example, one of the side faces of the rectangular section strand configurations shown in FIG. 12. It will be understood, however, that the invention contemplates that confection pieces can be made from two or more circular section strands, the final formed product having the discrete body parts and body part predetermined positionings as depicted, e.g., in FIG. 1a including the generally planar interfacing these present.

The arrangement of the rope sizers 34a, 34b and the in-feed frame 39 is such that the strand feeds are guided and converging so that the strands 32a, 32b come into close alongside juxtapositioning as at 44 and whereat the strand shaped faces confront juxtaposed in a predetermined orientation, i.e., the strands have planar edge faces (e.g., shaped thereon by roller pairs 38a, 40a) which have a registering disposition with each other. This orientation can be described as one wherein a reference or defined datum of the strand, i.e., the planar face shaped thereon, or if the strand be of circular cross section a vertical cutting plane passing through the strand, is disposed perpendicular to the forming die line travel movement of die members in the rotary forming machine and it is this strand orientation which must be maintained during following strand travel and up until actual confection piece formation takes place. Further advance of the now confronting strands 32a, 32b brings them to passage through a further or machine in-feed roller set 46, 48 which roller set can serve to concurrently final shape the strands to a particular cross-section geometry and also to force the inner strand confronting faces into cohered joinder along a common strand composite interface 50 forming a plural-stranded composite 51. This sequence of strand convergence and coherence movement is depicted in FIG. 12. FIG. 13 depicts the manner attending the coherence of two strands 32x and 32y along interface 50x. These strands it will be seen illustrate the instance where a planar surface 121 has been shaped on each strand with the remainder configuration of the strand cross section being of generally circular profile. Fully circular section strands 32p and 32t also can be used in making the confection products and in such instance the strands would be cohered only along a common tangential interface 131 as shown in FIG. 14.

The plural strand composite 51 now continues into the rotary forming machine and more specifically into the rotary forming section thereof denoted generally at 52 in FIG. 3 and shown in more detailed respects thereof in FIGS. 5 and 6. This post compositing travel will be through a guidance chute used to maintain proper strand orientation and which will be described in detail later, the chute positioning being shown in FIG. 4 but omitted from FIG. 3 for purposes of depiction clarity. As seen from FIG. 5 and as those skilled in the art known in respect of the Uniplast 160 machine, the rotary forming section 52 includes an eccentrically mounted rotating ring 54 including internal toothing 56 and a concentrically mounted rotating die head 58 fitted with external tooth like parts 59. The stranded composite 51 moves in chute guided travel from lead-in in a straight run to the forming section but makes transition to a circular travel course in the gap (as shown at 55 in FIG. 5) between the respective eccentric and concentric number members 54, 58. This gap closes or reduces as these two members pass the point of closest approach and they grab and pinch the composite until as is shown, they pinch or section same into individual composite pieces. These individual pieces in turn and as the die head 58 moves counterclockwise are engaged by cooperating horizontally disposed, oppositely acting straight line moving article forming dies 60, 62 (FIG. 6) and pushed into individual cavities 64 in a forming section plate member 66 so that the forming dies coming together compress and shape the individual composite piece in cooperation with cavity 64 to produce the shaped confection piece 10. After the successive individual confection pieces have been shaped, they are subjected to cooling to hasten body part solidification and they pass out of the forming operation into carry-off conveyor 70 for packaging etc.

In the confection piece forming operation shown in FIG. 3, the cohering joinder of strands 32a, 32b occurs at the entry of the strands to the forming machine 42 and concurrent with the passage of the strands between roller pair 46, 48 and these rollers additionally can serve to guide and confirm the intended final shape the strands and composite are to have, e.g., a rectangular cross section and they serve as well to provide desired strand orientation. It is also possible to delay joining the strands until just prior to the point where the strands would pass into the sectioning devices in the forming section 52 and as is seen from FIG. 4 wherein the apparatus parts corresponding to those shown in FIG. 3 have the same reference numerals but being depicted with less detail. From FIG. 4 it will be seen that the advancing strands 32a, 32b which have been preliminarily shaped in roller sets 38a, 40a to provide at least one planar face on each, pass into the forming machine with close positioning with each other but not in contact with each other. They pass around the rspective ones of roller pair 46, 48 for strand guidance and orientation but they are maintained apart as at 72 and they then each follow the straight run lead as seen in FIGS. 4 and 5 and then make transition to the upwardly directed circular travel course to make entry to the sectioning devices, this occurring at approximately 5 o'clock position of the forming section as viewed in FIG. 5. These strands then come together as at 74 to cohere them immediately before passing into the pinching grip of members 54, 48. During this last-mentioned travel from first entry of the strands to the forming machine until sectioning of the composite 51 occurs, it is as indicated before important that the strands be guided to maintain the proper and already established predetermined strand orientation thereof for joinder and also for composite presentation to the sectioning devices. In other words, the guidance keeps the strand datum as discussed earlier in connection with FIG. 3 perpendicular to the forming machine die travel line and prevents twist in the strands (or the composite in the FIG. 3 making operation). This guidance is effected with an improved form of machine guidance chute 80 fitted in place in the forming machine. The known Uniplast machine uses a similar type device but that device is not constructed to effect strand guidance in the manner required by the present invention since it serves only a strand course changing function and it allows strand twisting to occur. The guidance chute 80 (and with reference to FIGS. 8-11) has an initial straight length section 82 and makes transition to an upwardly curving fore end section 84 to provide strand entrance into circular travel path. The chute also makes lateral offset as at 86 to correspondingly translate the strand travel for positioning same to provide smooth entry alignment thereof with the sectioning devices inasmuch as these are relatively deeper in forming section 52 than the strand entry location to the machine. The FIGS. 8 and 9 chute embodiment is employed where the strands are cohered as a composite at entry to the forming machine (FIG. 3) and the FIGS. 10 and 11 chute embodiment is employed in the FIG. 4 forming operation where the strands enter the forming machine in separate paths and are cohered only as they arrive at the sectioning location.

The guidance chute constitutes a full enclosure strand guidance structure and is comprised of a bottom wall 81, spaced side walls 83, 87 upstanding from the wall 81 and a top or cover wall 89 secured against the top edges of the side walls 83, 87. The cover wall 89 it will be noted terminates proximal the entry of the strands or composite thereof into the pre-sectioning circular travel course transition. The chute preferably is constructed from stainless steel or brass material as these do not present any sticking problem for the high speed travelling strand or composite as it moves in contact with surfaces of the chute. It will be appreciated that the chute provides two-dimensional guidance for strands or strand composite passing therethrough. The side walls serve to guide in one dimension while the top and bottom walls effect guidance in the second direction. This enclosure of the strands or composite taken together with the high travel speed thereof prevents any twist or disorientation in the strand travel. The FIGS. 10, 11 chute includes a divider plate 85 depending from cover wall 89 which thereby divides the chute into separate chute courses associated with the travel of the separate strands 32a, 32b therethrough. The guidance chute will be sized to effect and maintain the established orientation of the strand or strand composite passing therethrough and accordingly the chute course dimensions will be such as to provide relative close enclosure about the strands or composite in the manner as shown, for example, in FIG. 11. The FIGS. 8 and 9 chute embodiment can have by, way of example, an inner chute width dimension of about ¾ inch and a height from bottom wall 81 to cover wall 89 of about ⅜ inch.

With respect to strand shaping and sizing, it is advantageous that at least one planar continuous face surface be provided on each strand. This can be effected by passing the batch former extruded cylindrically configured strand through a roller set that will flat shape one side of the strand. Advantageously, the strands will be shaped to provide each with a rectangular section as in the manner shown by FIG. 7 wherein a roller set 90, 92 shapes strand 32 in that fashion. As will be noted, the roller 90 has peripheral flanges 94 which make intersecting reception of a peripheral portion of roller 92 with the edge periphery of that roller 92, the face 93 of roller 90 and the parallel inner faces of flanges 94 defining at point of roller closest pass-by, a rectangular passage to correspondingly shape the plastic state strand material feeding through the roller set, the depicted shaping being the forming of a strand rectangular cross section. Where other strand cross-section configurations are intended, corresponding variations in the configuration of the shaping rollers will be made. If circular strands are to be cohered and product made therefrom, all of the rollers used will have circular edge configurations.

Strand sizes will of course depend on the material compositions being used as well as the numbers of body parts or layers the confection piece is to have. In connection with a two-layered product and rectangular strand configuration, a strand width for each of about 3/16 to about ½ inch and height of about 1.5 times the width to about 0.5 the width can be used. A composite of these could have a width of about 7/16 inch to about 13/16 inch and a height of about 1.5 times the width to about 0.25 times the width. In a preferred embodiment, the strand widths could be about ¼ inch to about ⅜ inch with a height of about 1.25 times the width to about 0.75 times the width. A composite in preferred form will have a width of about ½ inch to about ¾ inch and a height of about 0.75 times the width to about ¼ times the width.

The strand feeding operation is designed to allow high speed production of the confection pieces and strand speed therefore will be at line speeds in a range of about 110 feet to about 340 feet per minute and it is important that strand speed and strand viscosities be matched as closely as possible during the forming operations. Depending on the particular materials compositions involved, the strand plastic state temperatures at the forming operation will vary in an overall range of about 80° F. to about 200° F. For a hard candy composition the temperature range will be about 150° F. to about 190° F. and for chewy confection about 80° F. to about 120° F.

FIG. 15 illustrates another manner in which the plural discrete body part pieces can be shaped. A cohered vertically oriented two strand rectangular section composite 151 is fed in between two opposed drum units 152,153 each of which rotates about a fixed cam 154. Forming die members 155 arranged in a spaced radially directed array about each drum, engage the high points on the fixed cams to stroke the members 155 radially into cooperation one in each drum with one in the other drum as the drums pass the point of closest approach, these die members cooperating to compressively punch a confection piece from the composite. A chain type drop maker also could be used for production shaping.

It will be seen from the foregoing description that there is provided a highly advantageous confection piece form as well as a new manner in which the uniquely configured and structured confection piece can be made. Those skilled in the art will understand that certain variations and modifications can be made in respect of what has been disclosed herein and still be within the scope of the inventive concept disclosed.

What is claimed is:

1. An edible article of shaped body configuration comprised of at least two discrete body parts arranged in predetermined positioning one with respect to another and simultaneously formed as the solidified product of corresponding ones of separate stocks of plastic state edible materials compressively cohered together in a single compression step along common joinder interfaceing between each other, one body part being different from that of at least one other body part in respect of at least one of its physical and/or chemical properties, and wherein the body parts are substantially equal geometric volumes and are in the form of substantially staked layers.

2. The edible article of claim 1 in which the physical and/or chemical properties of one body part differ in respect of those of another part as to any one or a combination of its coloration, ingredient composition or texture.

3. The edible article of claim 2 in which the material of at least one body part is a confection.

4. The edible article of claim 3 in which the confection is one of hard candy, chewy confection and chewing gum.

5. The edible article of claim 4 in which the confection material of one body part is different than that of another body part.

6. The edible article of claim 1 in which the material in one body part includes a medicinal preparation comprising one of anesthetics, antitussives, antihistamines, antinauseants, decongestants or nutrients, another body part comprising a material normally interactive with the first body part material.

7. The edible article of claim 6 in which the said other body part contains an aldehyde-containing component.

8. The edible article of claim 7 in which the aldehyde is present as a component of a flavoring composition.

9. The edible article of claim 7 in which the material of said one body part includes a nutrient supplement and that of the other body part includes vitamin C.

10. The edible article of claim 9 in which the nutrient supplement is a basic compound.

11. The edible article of claim 10 in which the basic compound is calcium carbonate.

12. The edible article of claim 6 in which the material of said one body part and said other body part are medicinal preparations, that of the one body part normally being interactive with that in the other body part.

13. The edible article of claim 12 in which the material of said one body part includes aspirin and that of the other body part includes a decongestant or an antihistamine.

14. The edible article of claim 5 in which the material of said one body part is hard candy and that of the other body part is chewing gum.

15. The edible article of claim 5 in which the material of said one body part is hard candy and that of the other body part is chewy candy.

16. The edible article of claim 15 in which the chewy confection is a nougat.

17. The edible article of claim 5 in which the material of said one body part is chewing gum and that of the other body part is chewy candy.

18. The edible article of claim 2 in which the material of said one body part is different from that of said other body part in respect of the coloration of the two.

19. The edible article of claim 1 in which the layers are substantially planar coextensive.

20. The edible article of claim 2 in which the shaped body is comprised of at least three discrete body parts.

21. The edible article of claim 2 in which the shaped body is comprised of at least four discrete body parts.

22. A method for making an edible article of configuration having at least two discrete but unitarily joined parts, said method comprising advancing at least two separate plastic state continuous strands of edible material compositions from respective sources thereof along separate feed lines in passage directed toward a downstream article forming operation, the compositions in the respective sources being different one from another in respect of the at least one of their physical and/or chemical properties, converging and guiding the travel passage of the advancing strands such as to bring said strands into closely alongside confrontation with each other and establish a predetermined orientation of one with respect to the other, forming a continuous strand composite by coheringly joining the advancing strands along a common strand interface by moving the strands into contact with each other while maintaining the prior established orientation therebetween, sectioning the composite in a pre-shaping step to provide successive individual pieces, thereof, and then shaping each piece into an article configuration having discrete parts arranged in positioning corresponding to the cohered strand orientation.

23. The method of claim 22 in which the edible material sources differ one from another in respect of any one or a combination of coloration, ingredient composition or texture.

24. The method of claim 23 in which the plastic state continuous strands are advanced at substantially equal line speeds and matched viscosities.

25. The method of claim 24 in which the strand line speed is in a range of about 110 feet per minute to about 340 feet per minute.

26. The method of claim 23 in which the edible material compositions comprise confections.

27. The method of claim 26 in which the composite has a temperature at the forming operation in a range of about 80° F. to about 200° F.

28. The method of claim 27 in which at least one of the composite strands is a hard candy composition which at the forming operation is at a temperature in the range of about 150° F. to about 190° F.

29. The method of claim 27 in which at least one of the composite strands is a chewy confection composition which at the forming operation is at a temperature in the range of about 80° F. to about 120° F.

30. The method of claim 23 in which the respective plastic state strands are prior to being brought into close alongside confrontation with each other, subjected to a shaping operation to form a continuous planar face surface on each strand so that the thereafter established strand orientation presents such strand planar surfaces in facing confrontation, the cohering joinder of the strands being effected by bringing these planar surfaces into contact with each other.

31. The method of claim 30 in which the respective plastic state strands are coheringly joined remote from the forming operation.

32. The method of claim 31 in which the resepective plastic state strands are coheringly joined concurrently with the step of bringing said strands into alongside confrontation and establishment of predetermined orientation of the one with the other.

33. The method of claim 30 in which the respective plastic state strands are coheringly joined immediately prior to composite sectioning, the strands being guided during passage thereto from the location where the alongside confrontation and establishment of predetermined orientation was effected to maintain such orientation substantially unaltered as the composite is being sectioned.

34. The method of claim 22 in which the respective plastic state strands prior to coheringly joining same are subjected to a shaping operation which shapes each into a strand of rectangular cross section.

35. The method of claim 34 in which the respective strand cross sections each have a width in the range of about ⅜ inch to about ⅛ inch and a height in a range of about 1.5 times the width to about 0.5 times the width.

36. The method of claim 35 in which the strand width is in the range of about 3/16 inch to about ⅛ inch.

37. The method of claim 35 in which the strand width is in the range of about ⅜ inch to about ¼ inch and the height is in a range of about 1.25 times the width to about 0.75 times the width.

38. The method of claim 34 in which the stranded composite has a cross section the width of which is in the range of about 7/16 inch to about 13/16 inch and a height in the range of about 1.5 times the width to about 0.25 times the width.

39. The method of claim 38 in which the composite width is in the range of about ½ inch to about ¾ inch and the height is in the range of about 0.75 inch to about 0.25 inch.

40. The method of claim 23 in which the composite is sectioned such as to provide individual pieces thereof having a weight in a range of about 3 grams to about 20 grams.

41. The method of claim 22 in which the forming operation is effected with a rotary forming device, the strand composite transiting a circular travel course during the sectioning thereof into individual composite pieces, the individual pieces being maintained in the same strand orientation as that of the composite, the pieces being shaped with oppositely acting straight line moving cooperating die members which close about each piece and uniformly compressively shape the piece into article configuration.

42. A method for making an edible article of configuration having at least two discrete but unitarily joined parts, said method comprising advancing at least two separate plastic state continuous uniformly thick strands of edible material compositions from respective sources thereof along codirectional feed lines, the compositions in the respective sources being different one from another in respect at least one of its physical and/or chemical properties, cohering the two strands along a planar common joinder interfacing therebetween to form a composite of coextensively disposed strands, and thereafter passing the composite through a forming device which acts crosswise to the composite joinder interface to compressively shape at least a portion of the composite into an article having uniformly thick discrete parts arranged in positioning corresponding to that of the strands in the composite.

43. The method of claim 42 in which the forming device comprises a pair of oppositely acting cooperating die members which move in a straight line forming course disposed substantially perpendicular to the planar interfacing of the stranded composite.

44. The method of claim 42 in which the forming device comprises a drop maker roller assembly.

45. In a rotary candy forming machine of the type wherein at least one continuous plastic state strand of a confection composition having a predetermined strand orientation is moving in a generally straight line lead-in-path at entry to the machine and is then sectioned into pieces by a sectioning means carried in the machine following strand transition from straight line travel to travel in a circular path within the machine, and the pieces are thereafter shaped by moving cooperating shaping members acting crosswise to the circular path, the improvement of a strand travel guidance chute extending from the strand machine entry location to proximal the sectioning means, the chute including an initial length straight section and a curved fore length section for directing the strand into curved travel transition, the chute having side wall means closely embracing the travelling strand to inhibit twisting of said strand from said orientation.

46. The improvement of claim 45 in which the chute comprises an enclosure structure having spaced apart side walls and spaced bottom and cover walls connected therewith.

47. The improvement of claim 46 wherein the chute comprises at least two separate chute guidance courses each accommodating a separate continuous plastic state strand, and effective to maintain said strands in the said predetermined orientations thereof.

48. The improvement of claim 47 in which the separate chute guidance courses are defined by a longitudinal divider plate extending between the chute bottom and cover walls.

49. In apparatus which includes means for forming plural plastic state strands of edible composition, and means for shaping and advancing said strands toward an article forming operation, said shaping and advancing means imparting a predetermined advance orientation to said strands related to required entry dispositions thereof to an article forming device downstream of said shaping and advancing means, the improvement of strand orientation guidance means disposed between the shaping and advance means and the article forming device effective to engageably guide and hold said strands in the said predetermined advance orientations thereof so that said strands enter the forming device undeviated from such orientations.

50. The improvement of claim 49 in which the guidance means comprises a chute means closely embracing the strands.

51. The improvement of claim 50 in which the chute means comprises a single enclosed chute structure, the chute structure including a divider wall therein defining separation chute courses associated with the respective strands.

52. In appaatus which includes means for forming and advancing at least two continuous plastic state strands of edible material compositions to a forming machine which sections and shapes the strand in-feed thereto into individual edible articles, tne strands being cohered together along a common interface as a stranded composite prior to the sectioning in said forming machine, the improvement of strand shaping means for shaping at least one continuous planar surface on each continuous strand prior to its cohering joinder to the other so that the strands can thereafter being juxtaposed alongside each other with the planar surface of one facing that of the other and cohered joinder be effected by merging said planar surfaces into face-to-face contact.

53. The improvement of claim 52 in which said shaping means comprises a pair of cooperating shaping rollers associated with each strand, at least one of said rollers in each pair having a straight peripheral edge against which the associated strand passes infeed through a nip defined by said roller pair.

54. The improvement of claim 53 in which the other roller in each pair is provided with a straight peripheral shaping edge whereby planar surfaces are shaped on opposite sides of the strand passing through the roller pair defined nip.

55. The improvement of claim 54 in which one of said rollers in each pair includes flanges extending radially beyond its straight peripheral edge to define a space receptive of a peripheral edge portion of the other roller in the pair whereby inner face parts of the flanges effect additional shaping of the strand passing through the roller nip.

56. A method for making an edible article of configuration having at least two discrete but unitarily joined parts, said method comprising advancing at least two separate plastic state continuous strands of edible material compositions from respective sources thereof along codirectional feed lines, the compositions in the respective sources being different one from another in respect at least one of its physical and/or chemical properties, converging the strands in closely alongside positioning one with the other in a predetermined orientation of one with respect to the other, and thereafter passing the strands in that close alongside positioning and predetermined orientation through a forming device which acts crosswise to the strand advance to compressively shape at least a portion of the strands into an article having discrete parts arranged in positioning corresponding to that of the strands.

57. An edible article made by the method of claim 22.
58. An edible article made by the method of claim 23.
59. An edible article made by the method of claim 26.
60. An edible article made by the method of claim 30.
61. An edible article made by the method of claim 34.
62. An edible article made by the method of claim 35.
63. An edible article made by the method of claim 38.
64. An edible article made by the method of claim 40.

* * * * *